(12) United States Patent
Wilson

(10) Patent No.: US 7,817,354 B2
(45) Date of Patent: Oct. 19, 2010

(54) PANORAMIC IMAGING SYSTEM

(75) Inventor: Gordon Cook Wilson, San Francisco, CA (US)

(73) Assignee: Capsovision Inc., Saratoga, CA (US)

( * ) Notice: Subject to any disclaimer, the term of this patent is extended or adjusted under 35 U.S.C. 154(b) by 415 days.

(21) Appl. No.: 11/624,209

(22) Filed: Jan. 17, 2007

(65) Prior Publication Data

US 2008/0100928 A1     May 1, 2008

Related U.S. Application Data

(60) Provisional application No. 60/862,973, filed on Oct. 25, 2006.

(51) Int. Cl.
*G02B 13/06* (2006.01)
*G02B 5/04* (2006.01)
(52) U.S. Cl. ...................................... 359/725; 359/834
(58) Field of Classification Search ................. 359/725, 359/726, 833, 834, 648, 649; 348/36
See application file for complete search history.

(56) References Cited

U.S. PATENT DOCUMENTS

2005/0151837 A1\* 7/2005 Cutler ......................... 348/36
2006/0217593 A1\* 9/2006 Gilad et al. ................. 600/160

\* cited by examiner

*Primary Examiner*—Alicia M Harrington
(74) *Attorney, Agent, or Firm*—Brosemer, Kolefas & Associates

(57) ABSTRACT

An optical imaging system and method for producing panoramic images exhibiting a substantial field of view.

10 Claims, 13 Drawing Sheets

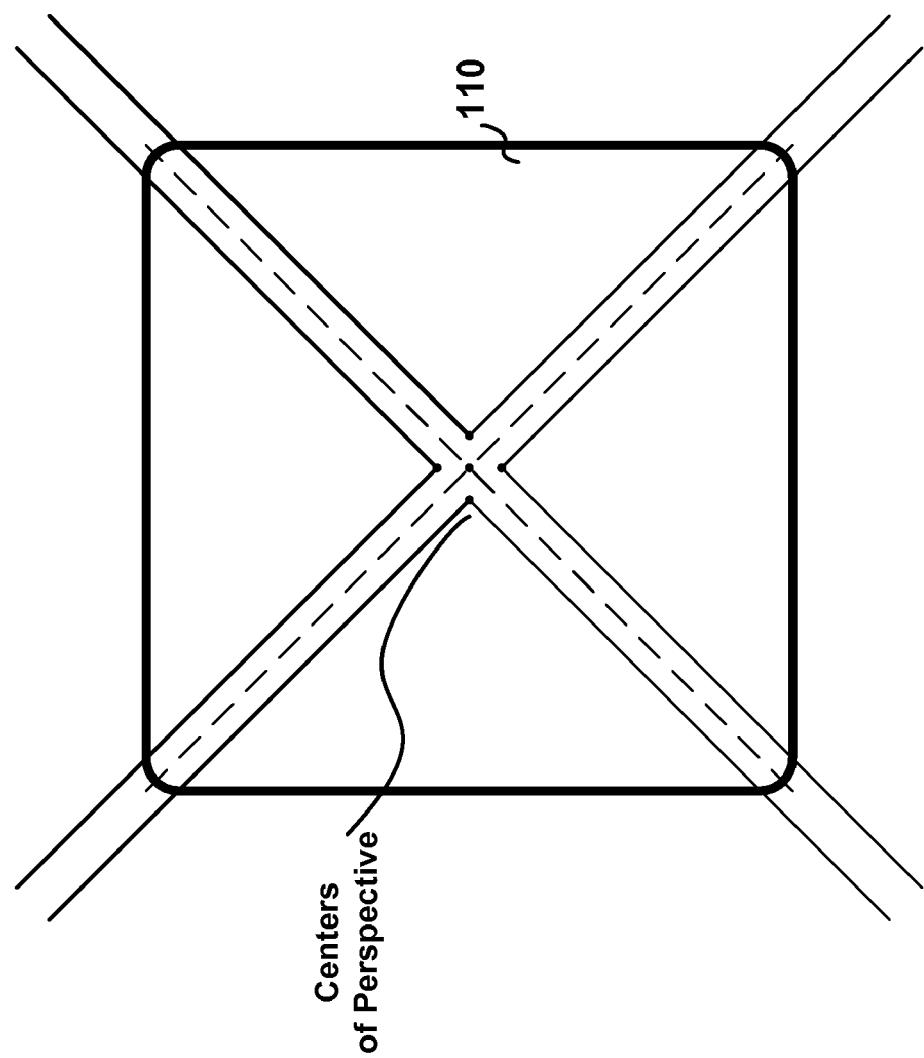

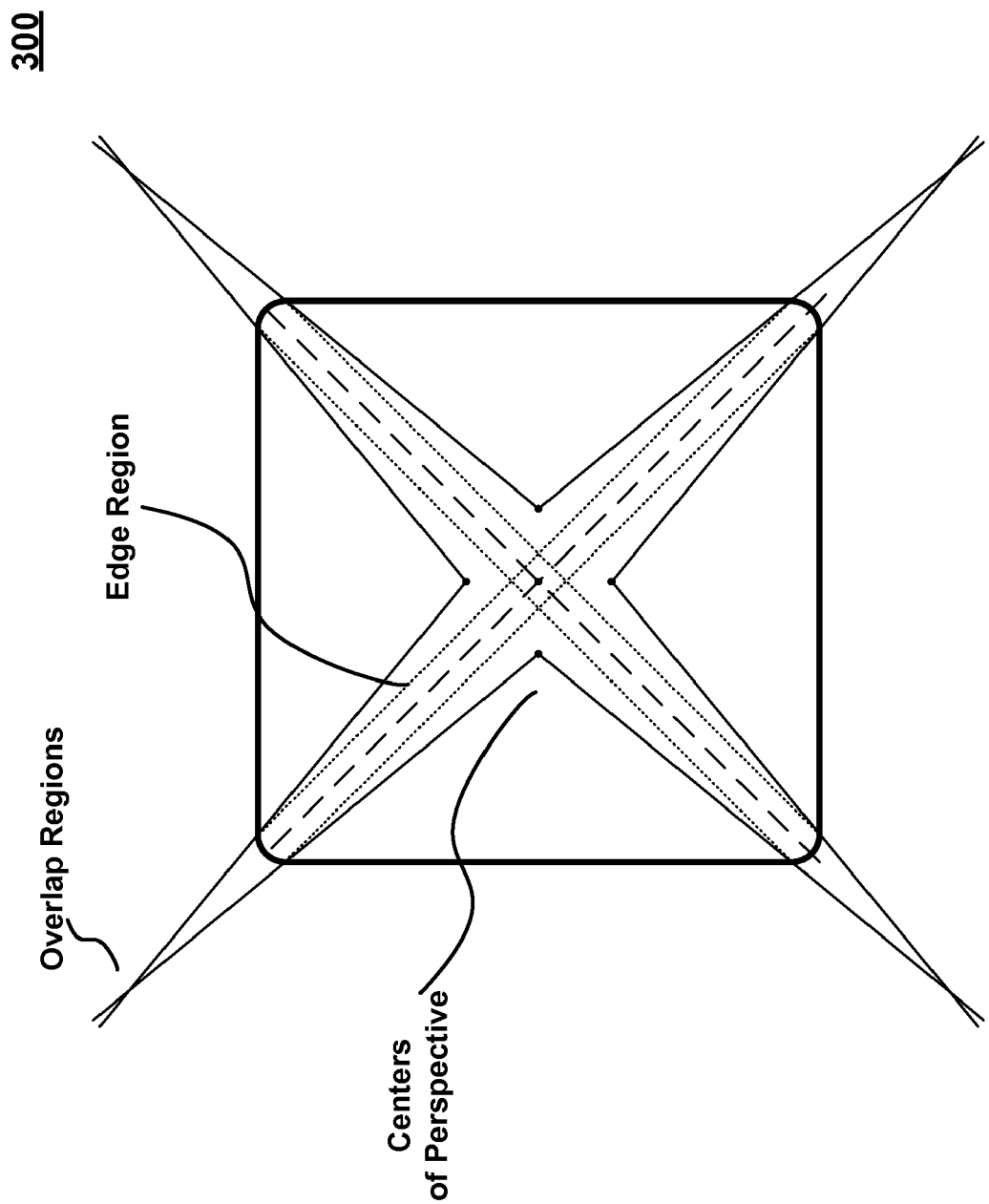

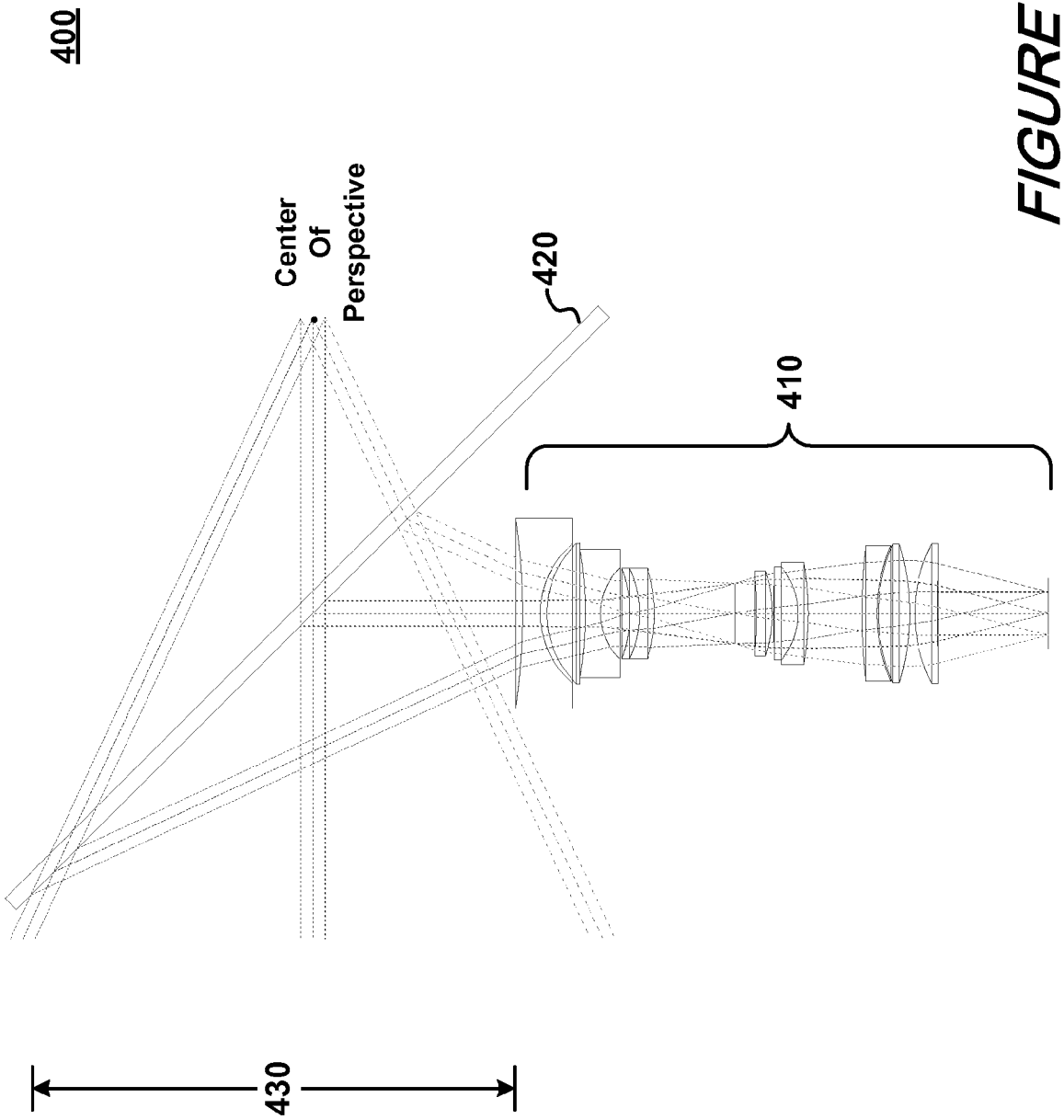

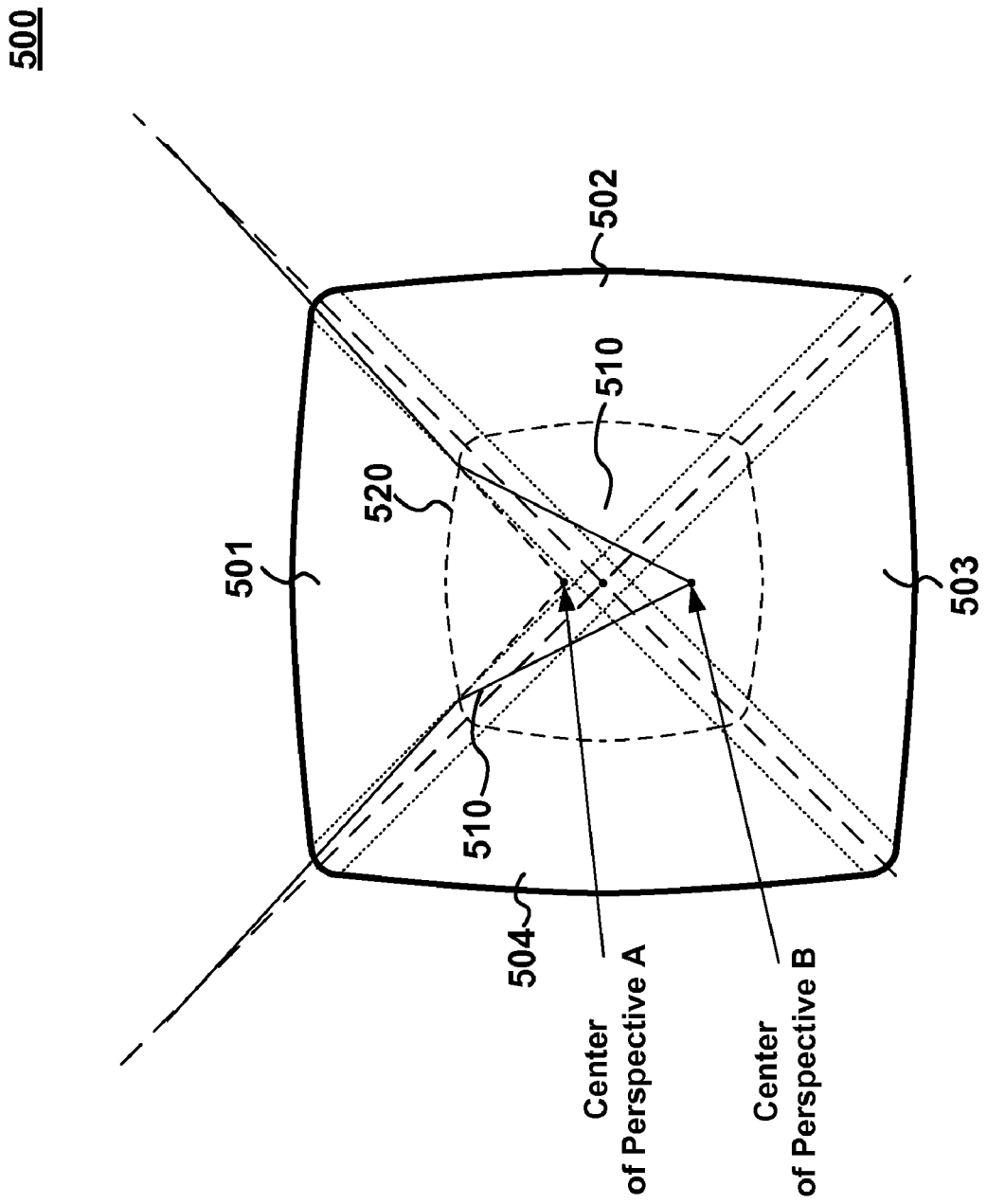

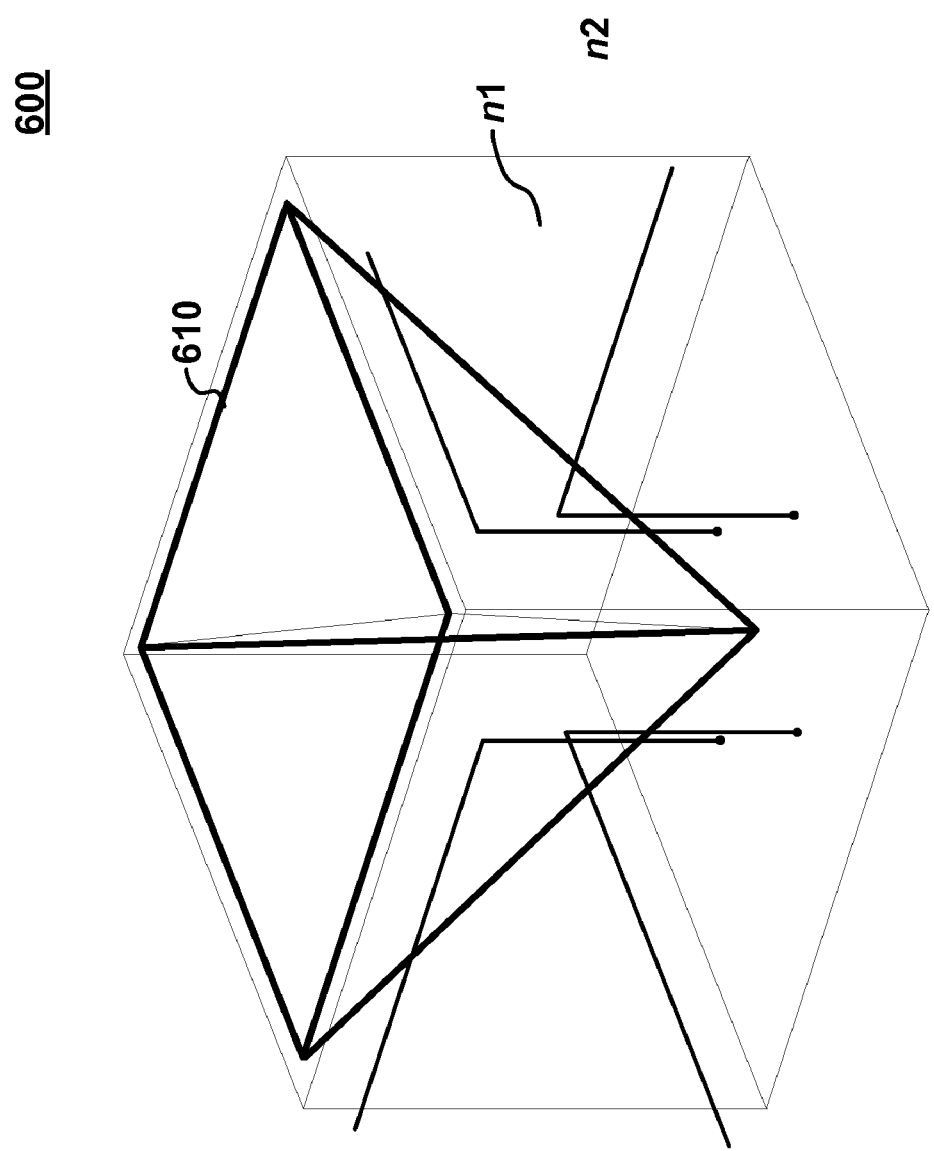

PANORAMIC IMAGING SYSTEM

CROSS REFERENCE TO RELATED APPLICATIONS

This application claims the benefit of U.S. Provisional Application No. 60/862,973 filed 25 Oct. 2006, the entire file wrapper contents of which are incorporated by reference as if set forth at length herein.

FIELD OF THE INVENTION

This invention relates generally to the field of optical imaging and in particular to a composite panoramic imaging system that provides overlapping fields of view such that a composite image may encompass a full 360° field of view.

BACKGROUND OF THE INVENTION

In a number of applications the ability to generate a panoramic image exhibiting a substantial field of view e.g., 360° is of great utility. Efforts to date that provide such panoramic images oftentimes involve complicated arrangements of multiple cameras, sophisticated image processing software or combinations thereof.

SUMMARY OF THE INVENTION

One embodiment of the present invention provides a panoramic imaging system that produces a composite panoramic image exhibiting a substantial field of view, e.g., 360°. Advantageously a system constructed according to the present invention needs only a single image sensor to provide a panoramic image. In addition, a system so constructed according to the present invention may advantageously exhibit a substantially larger vertical field of view (VFOV) than prior art systems of comparable size.

In sharp contrast to the prior art multi-camera configurations, an apparatus constructed in accordance with the present invention does not merely reflect or redirect the fields-of-view of a plurality of imagers (cameras) as done in the prior art multi camera configurations. Rather, a reflective apparatus constructed according to the present invention is effectively a part of an imager's optical objective.

Viewed from a first aspect—the present invention is directed to an arrangement employing a pyramid with convex faces to provide a panoramic field of view to a camera or other imaging system.

Viewed from another aspect—the present invention is directed to an arrangement employing a pyramid immersed or suitably enveloped in a high refractive index transparent material such as glass or plastic to provide a panoramic field of view to a camera or other imaging system.

Viewed from still another aspect—the present invention is directed to a method of producing a panoramic image and images so constructed.

Viewed from yet another aspect—the present invention is directed to an encapsulated panoramic imaging system exhibiting a suitably small size, modest power requirement and panoramic imaging capability for numerous in-vivo applications.

BRIEF DESCRIPTION OF THE DRAWING

A more complete understanding of the present invention may be realized by reference to the accompanying drawing in which:

FIG. 2 shows a schematic of the bottom view of the pyramid of FIG. 1 wherein the centers have been shifted relative to what is shown in FIG. 1;

FIG. 3 shows a schematic of the bottom view of the pyramid depicting the centers of perspective moving further from the central axis of the pyramid of FIG. 1;

FIG. 4 shows a schematic showing a retrofocus wide-angle lens positioned below one face of the pyramid;

FIG. 5 shows a schematic bottom view of a pyramid having reflective convex faces according to the present invention;

FIG. 6 shows a schematic of an alternative embodiment of the pyramid immersed in a high index transparent material according to the present invention;

DETAILED DESCRIPTION

The following merely illustrates the principles of the invention. It will thus be appreciated that those skilled in the art will be able to devise various arrangements which, although not explicitly described or shown herein, embody the principles of the invention and are included within its spirit and scope.

Furthermore, all examples and conditional language recited herein are principally intended expressly to be only for pedagogical purposes to aid the reader in understanding the principles of the invention and the concepts contributed by the inventor(s) to furthering the art, and are to be construed as being without limitation to such specifically recited examples and conditions.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

By way of further background and as known in the art, a panoramic imaging system may include a plurality of cameras with contiguous fields-of-view such that a composite image covers a full 360°. If each of the cameras shares a virtual center of perspective, then a seamless and natural-looking composite image can be formed without employing computationally intensive algorithms. For applications such as real-time video recording, transmission, and display, such low computational overhead is beneficial.

U.S. Pat. No. 5,745,305 describes such a panoramic viewing system in which several cameras have a common optical center (center of perspective). As described therein, the field of view (FOV) of each camera is redirected by one face of a reflective pyramid having 45° side inclination(s). If folded centers of perspective, lying on the optical axis folded by the mirrors, are positioned in a common plane with the pyramid apex, then the mirror-image optical centers are coincident.

Figure 1:
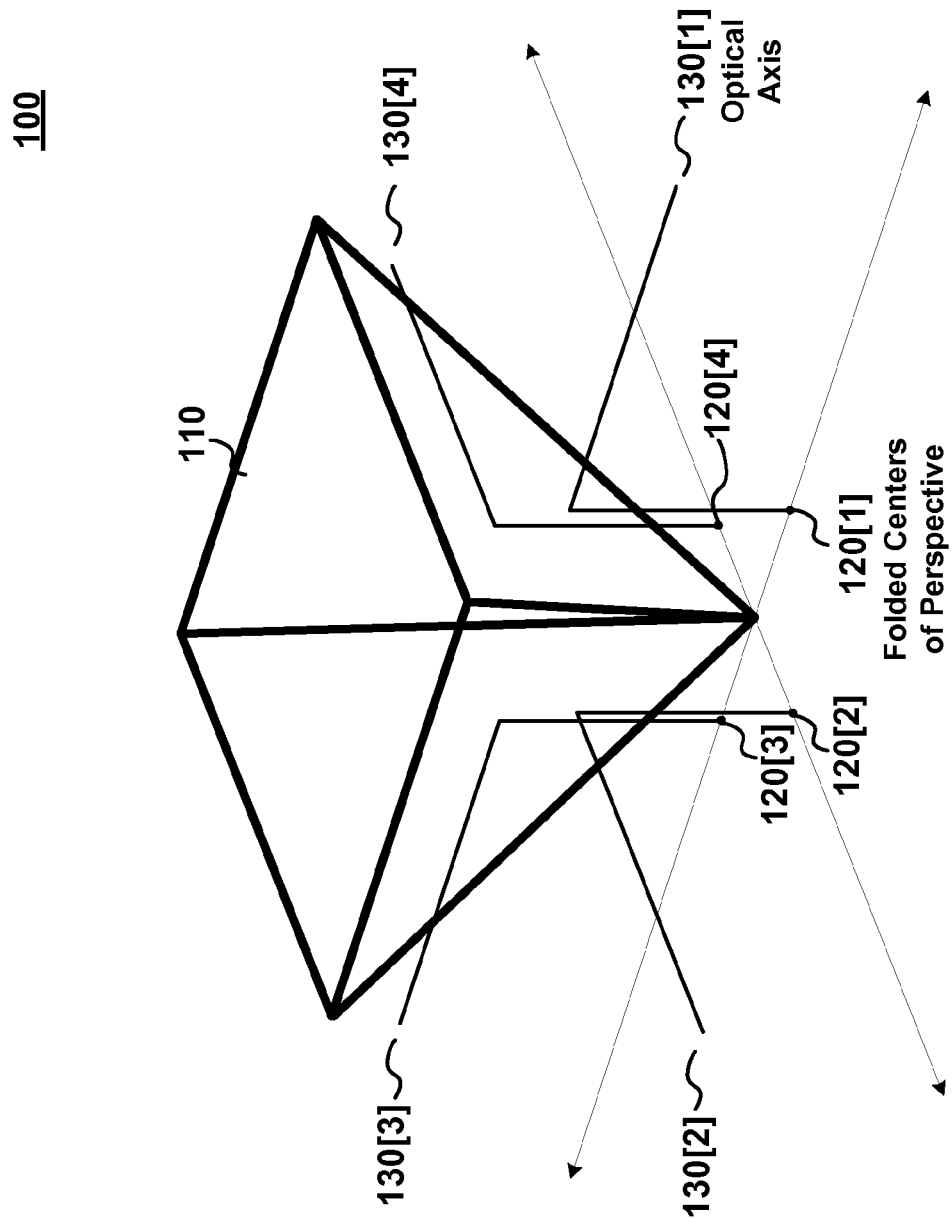
FIG. 1 shows a schematic of a four-sided reflective pyramid and folded centers of perspective and optical axes associated with four cameras.

An understanding of these principles may be enhanced with reference to FIG. 1 which shows in schematic a four-sided reflective pyramid 110 and four folded centers of perspective 120[1] ... 120[4] at which entrance pupils of individual cameras (not specifically shown) may be positioned. Each of the cameras so positioned has an optical axis associated therewith that is folded by the reflective facets of the pyramid. For each camera, a line coincident with the optical axis before it folds passes through the center of perspective at a point beyond the fold mirror and the optical axis after it folds passes through the folded center of perspective. Each of the folded optical axes 130[1] ... 130[4] defines a half plane with vertical edge, and the four half planes are separated by 90° of rotation about the central axis of the pyramid. Consequently, if individual cameras positioned at a respective folded center of perspective 120[1] ... 120[4] each has a horizontal field-of-view (HFOV) of at least 90°, then a composite HFOV constructed from the combined individual fields-of-view is 360°.

As recognized by those skilled in the art, the edges of the pyramid 110 in such a configuration cannot be made infinitely sharp. Consequently a portion of the HFOV is lost due to the finite radius of curvature, chamfer, or chipping on the edge.

U.S. Pat. Nos. 6,111,702 and 6,700,711 disclose one approach to eliminate the edges from the FOV whereby the folded centers of perspective are raised above the plane containing the apex of the pyramid such that the virtual optical centers (centers of perspective) are displaced outward from the center of the pyramid.

With that approach in mind and turning our attention now to FIG. 2, there it shows a bottom view of the pyramid 110 which was earlier described and shown in FIG. 1. As can be understood, light rays at the extrema of an individual 90° HFOV do not reflect in the non-planar edge. Therefore the 90° HFOV is maintained but the centers-of-perspective are not coincident and the composite image has blind regions equal to twice the center-of-perspective displacement.

For large conjugate ratios (distantly viewed objects), the difference in parallax from a camera positioned at a particular center of perspective to a next camera positioned at the next center of perspective is negligible and any gaps are small relative to the overall scene dimensions (object height). For example, a 2 mm blind region may not be particularly noticeable when viewing a scene 100 m away.

For certain potentially useful applications of panoramic imaging systems such as endoscopes, capsule endoscopes, and boroscopes, however, the conjugate ratio is not particularly large as distant objects are not observed in these applications. More specifically, a conjugate ratio in such applications may be well under 100 or even under 10. For situations exhibiting a low conjugate ratio, any blind regions are no longer an unnoticeable fraction of the total object imaged. Compounding this is the fact that any difference in parallax is now more noticeable as well.

FIG. 3 shows a further view of the bottom of the pyramid previously described. As can be observed from this FIG. 3, the blind region may be eliminated by moving the centers of perspective further from the central axis of the pyramid. If cameras used with a system exhibiting these moved centers of perspective have a HFOV slightly in excess of 90° then the fields of view will sufficiently overlap and the blind region will only extend a limited distance from the pyramid corners.

Turning our attention now to FIG. 4, there it may be seen that moving the folded centers or perspective up closer to the pyramid faces has the undesirable effect of reducing the vertical field of view (VFOV). More particularly, FIG. 4 shows a schematic of a retrofocus wide-angle lens assembly positioned below one face 420 of the pyramid. In this example shown in FIG. 4, a camera 410 will have a horizontal FOV (HFOV) of substantially 90° but its VFOV is limited to approximately 50° by the first element of the lens itself and the finite height of the pyramid face 420 (mirror). Moving the lens up towards the pyramid face 420, thereby shifting the center of perspective outward, would further reduce the VFOV.

For the example in FIG. 4, the ratio of the mirror height (430)—defined as the vertical distance from that surface of the lens closest to the mirror to the top of the mirror—to the focal length of the lens is defined by $\Gamma=9.4$. As can be appreciated, the VFOV may be increased by increasing $\Gamma$. However, this adds cost, and for applications such as those identified earlier e.g., endoscopy, the additional space required for a larger pyramid (mirror) may not be available.

According to an aspect of the present invention, if $\Gamma$ is decreased a larger vertical field of view is achievable with a physically smaller system.

Turning now to FIG. 5, there it shows a bottom view of a pyramidal structure 500 according to one aspect of the present invention. More particularly, each of the reflective four faces (501, 502, 503, 504) of the pyramid 500 are convex. For example, each of the reflective faces may be spherical convex or they may be cylindrical convex wherein the axis of the cylinder (for example) is inclined 45° relative to the central axis of the pyramid 500. Furthermore, and according to an aspect of the invention, the reflective faces 501, 502, 503, and 504 may be biconic, aspherical, acylindrical, or other convex shapes as long as the intersection of the convex surface and a horizontal plane defines an outward-curved line 520 relative to the central axis of the pyramidal structure 500.

With continued reference to that FIG. 5, shown therein are the outermost rays 510 of the horizontal field of view for a single camera (not specifically shown). The intersection of a plane containing the rays coming from the object side with the mirror (reflective face) is shown as a dotted line 520. Two centers of perspective A and B are shown. As can be observed from this FIG. 5, the actual center of perspective is shifted from point B to point A through the effect of the curvature of the mirror (reflective face), thus allowing the camera to be positioned lower, by a distance substantially equal to distance AB, while allowing a camera having a lens with a reduced FOV to be used.

FIG. 6 illustrates another configuration according to the principles of the invention wherein a reflective pyramid 610 is sufficiently immersed or otherwise enveloped by a high-refractive-index transparent material (e.g., glass or polymer)

having an index of refraction n1. Reflection may be achieved by one or more dielectric interfaces or metals at the pyramid faces.

FIG. 7 shows a bottom view of the immersed pyramid of FIG. 6. With reference to that FIG. 7, we see the medium immersing the pyramid 700 is, in turn, immersed in an outer medium 720 wherein light rays 710 converge more rapidly in the outer medium (i.e., air) having an index of refraction n2 than in an inner medium having an index of refraction n1, where n1>n2. As a result, and as can be observed in this FIG. 7, the optical center (center of perspective) is moved from point B to point A as a result of the refraction produced at interface 715. Advantageously—with such a configuration—that portion of the optical objective on the image side of the fold mirror need accept a range of ray angles less than the FOV and the first surface of optical power after the fold mirror may be positioned a distance lower than it would be in the case where n1=n2, while still achieving an optical center of perspective at point A.

Figure 7A:
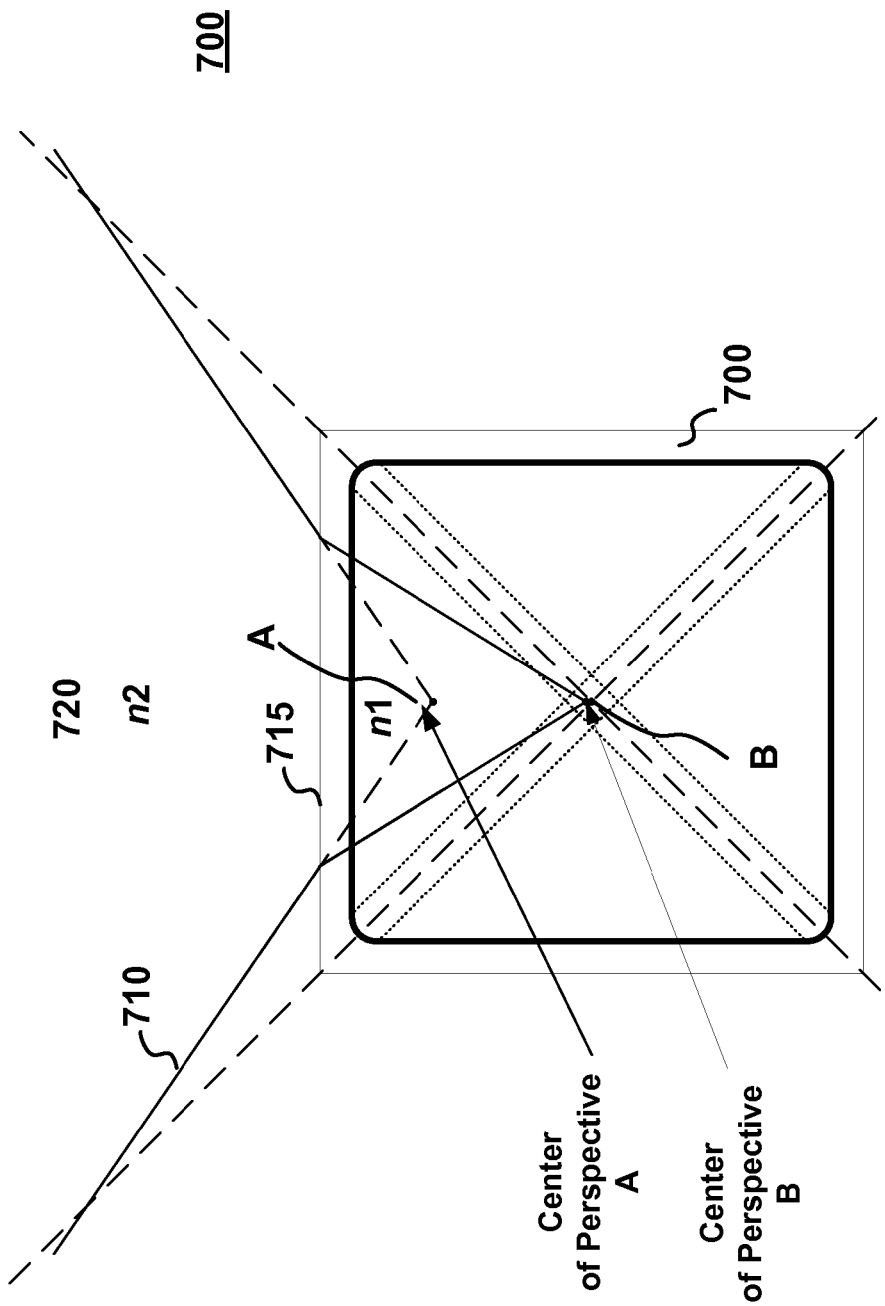
FIG. 7a shows a schematic of light rays converging in the high index transparent material of FIG. 6.

As can be further observed from this FIG. 7a, the center of perspective at point A, lies well forward of the central axis of the pyramid 700. Additionally, it may be observed that when a pyramid 700 is so immersed within an immersion medium having index of refraction greater than that of the medium surrounding the immersion medium, the light rays 710 in the immersion medium converge toward a point B which—in this case—is just in front of the pyramidal axis (not specifically shown.).

Figure 7B:
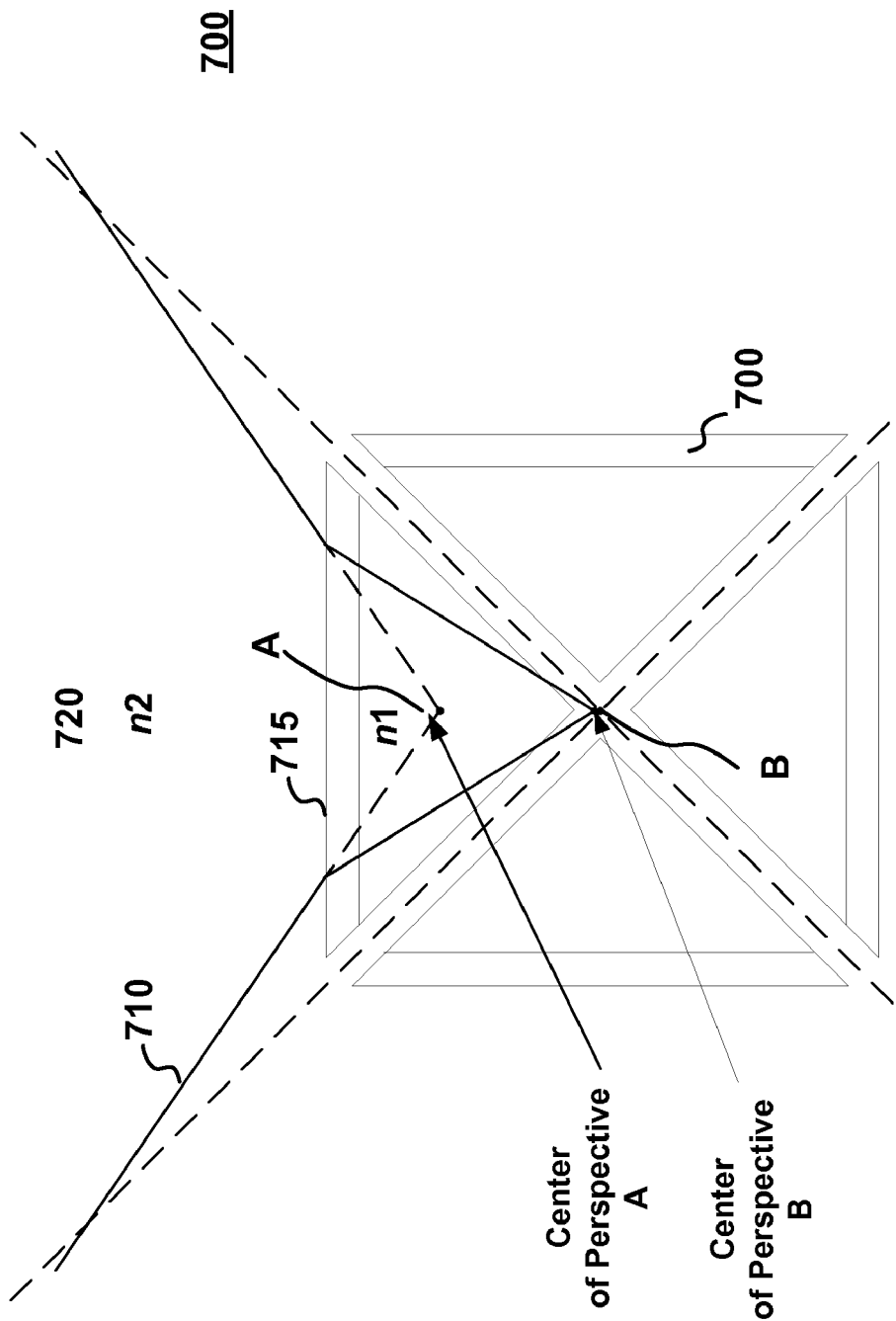
FIG. 7b shows a schematic of light rays converging in the high index transparent material of FIG. 6 wherein a number of prisms are arranged such that their reflective faces lie on the faces of an imaginary pyramid and the immersing medium is shown divided into four (4) parts.
Figure 8:
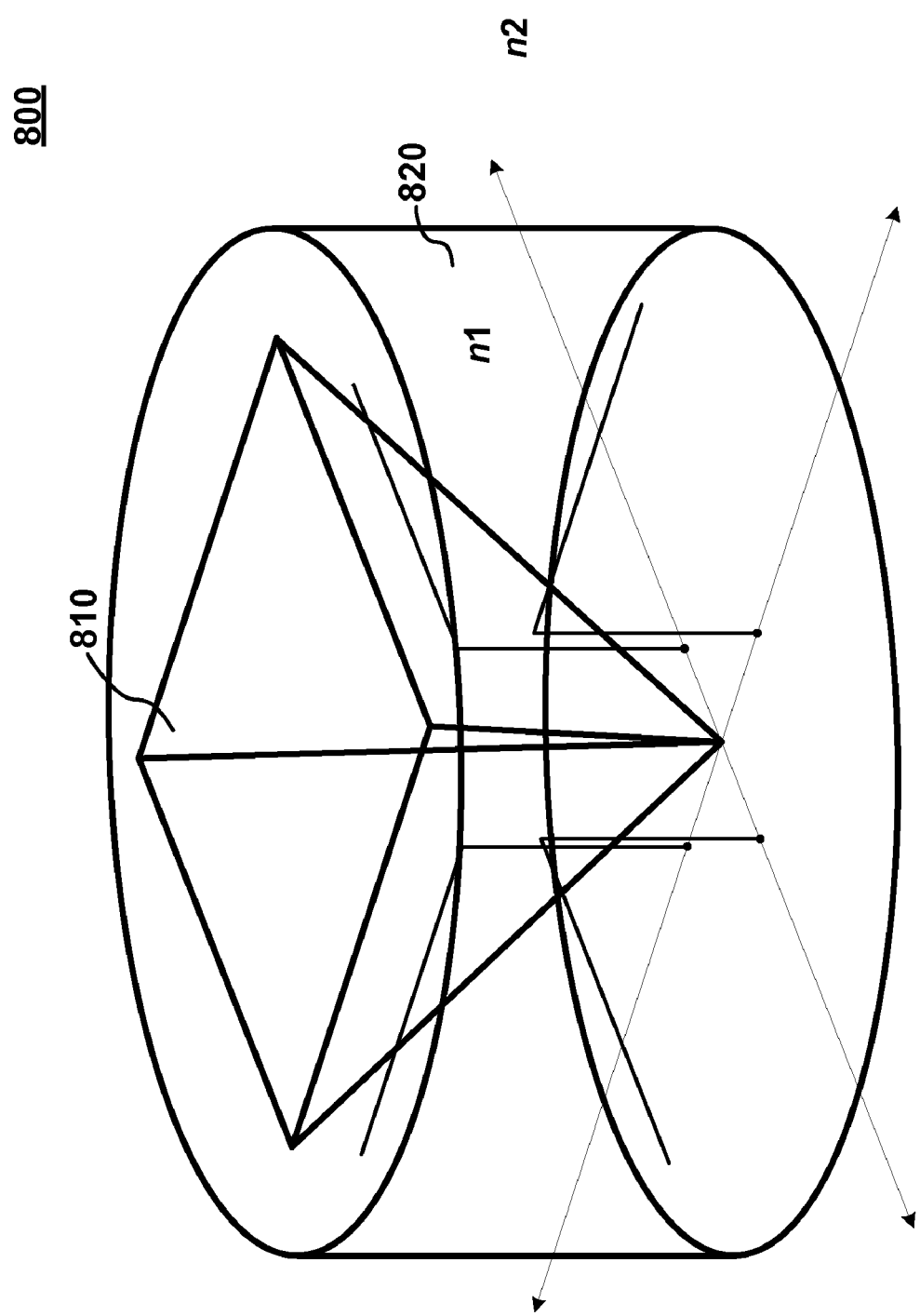
FIG. 8 shows a schematic of an alternative embodiment of the pyramid environment.

As can be appreciated by those skilled in the art, while the present invention has been shown specifically including a pyramid, the invention is not so limited. By way of additional example and not limitation, it is noted that a collection of reflective surfaces may be arranged such that their collective arrangement is substantially pyramidal in shape. In this manner, the same or different reflective surfaces may be employed, or different media having different (or the same) refractive index may further immerse the reflective structures. Advantageously, a different media may be used to immerse different reflective surfaces. As an illustration of these concepts, FIG. 7b shows a schematic of light rays converging in the high index transparent material of FIG. 6 wherein a number of prisms are arranged such that their reflective faces lie on the faces of an imaginary pyramid and the immersing medium is shown divided into four (4) parts;

FIG. 8 shows a schematic illustration of an immersed pyramid configuration 800 in which a pyramid 810 is immersed in or otherwise enveloped by another material 820 having a refractive index n1. This medium is surrounded by a second medium of lower refractive index n2. Advantageously, and as shown in this FIG. 8, the overall shape of this other material 820 need not be rectangular, i.e., it may have curved faces or be cylindrical as shown in the figure or any other shape as well. As can be appreciated however, a sphere may not move the optical center appreciably since most light rays will pass through its surface at normal, or near-normal incidence. Nevertheless, a material having a higher refractive index of any shape surrounding the pyramid 810 reduces the cone angle within the immersion medium for rays from any field point.

Notwithstanding the above, finite edge regions may vignette at the edges of the HFOV. For example, in FIG. 3 shown and described previously, the chief ray clears the edge region. However, one half of the rays emanating from the same field point will strike the edge region and be vignetted. To eliminate this vignetting, the centers of perspective must be moved even further from the center of the pyramid. Fortunately, and according to a principle of the present invention, immersing the pyramid into a high-index medium reduces the cone angle within the medium for a given object space numerical aperture (NA) and thereby reduces the distance that the virtual centers must be shifted from the center of the pyramid to avoid vignetting.

Figure 9:
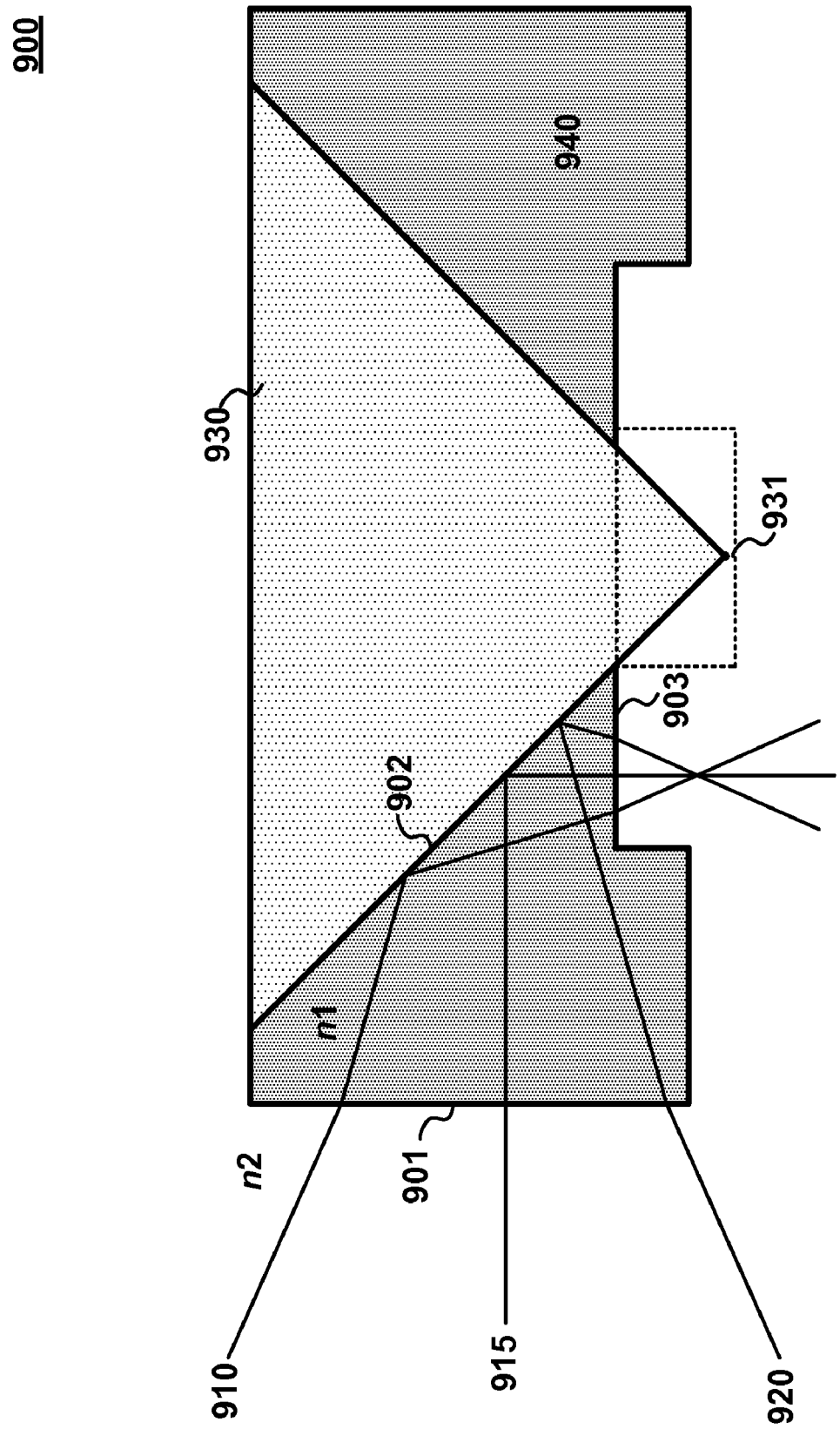
FIG. 9 shows a schematic of a cross-sectional side view of an immersed pyramid configuration according to an aspect of the present invention.

FIG. 9 shows a side cross-sectional view of an immersed pyramid and three chief rays 910, 915, 920. As shown, the pyramid 930 is immersed in refractive media 940 having an index of refraction n1 that is in turn surrounded by a medium of index n2. As shown and may be readily understood by those skilled in the art, the pyramid 930 need not physically extend to its apex 931 as no light rays within the FOV strike that portion of the pyramid 930 shown in the figure within the dotted area adjacent the apex.

As shown in this FIG. 9, the immersed configuration shown results in three interfaces at which each of the rays 910, 915, 920 are either refracted or reflected as they proceed from object space to image space. As can be observed, the three interfaces include refractive interface 901, reflective interface 902 and refractive interface 903.

Figure 10:
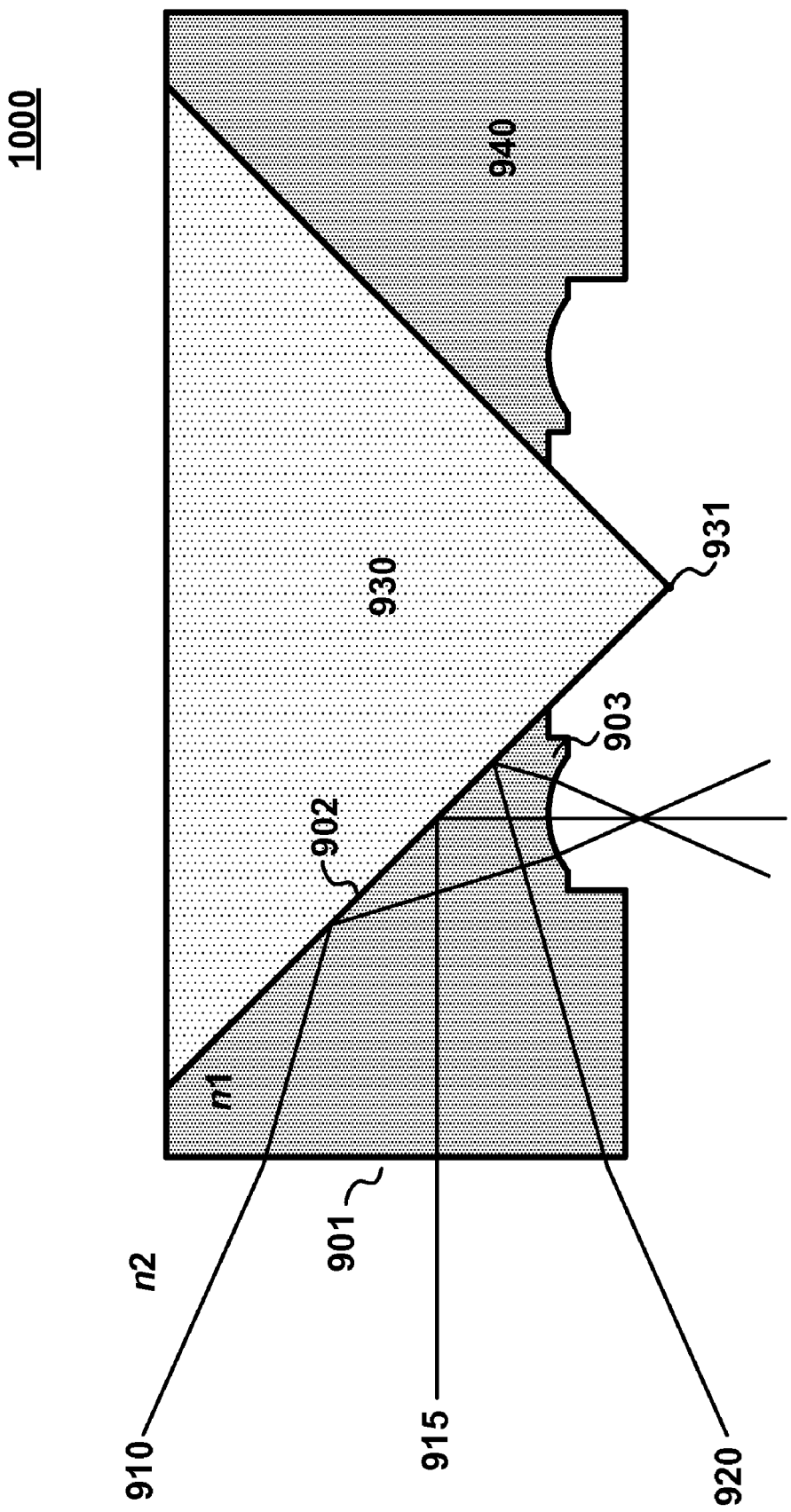
FIG. 10 shows a schematic of an alternative embodiment of the immersed pyramid configuration of FIG. 9 where the immersive medium exhibits a negative curvature according to an aspect of the present invention.

Advantageously, the immersive medium (object) will act as a lens if either the first 901 or third 903 interfaces shown are curved. As shown in FIG. 10, this third interface 903 exhibits a negative curvature and as a result the immersive object 940 is said to have negative power.

Figure 11:
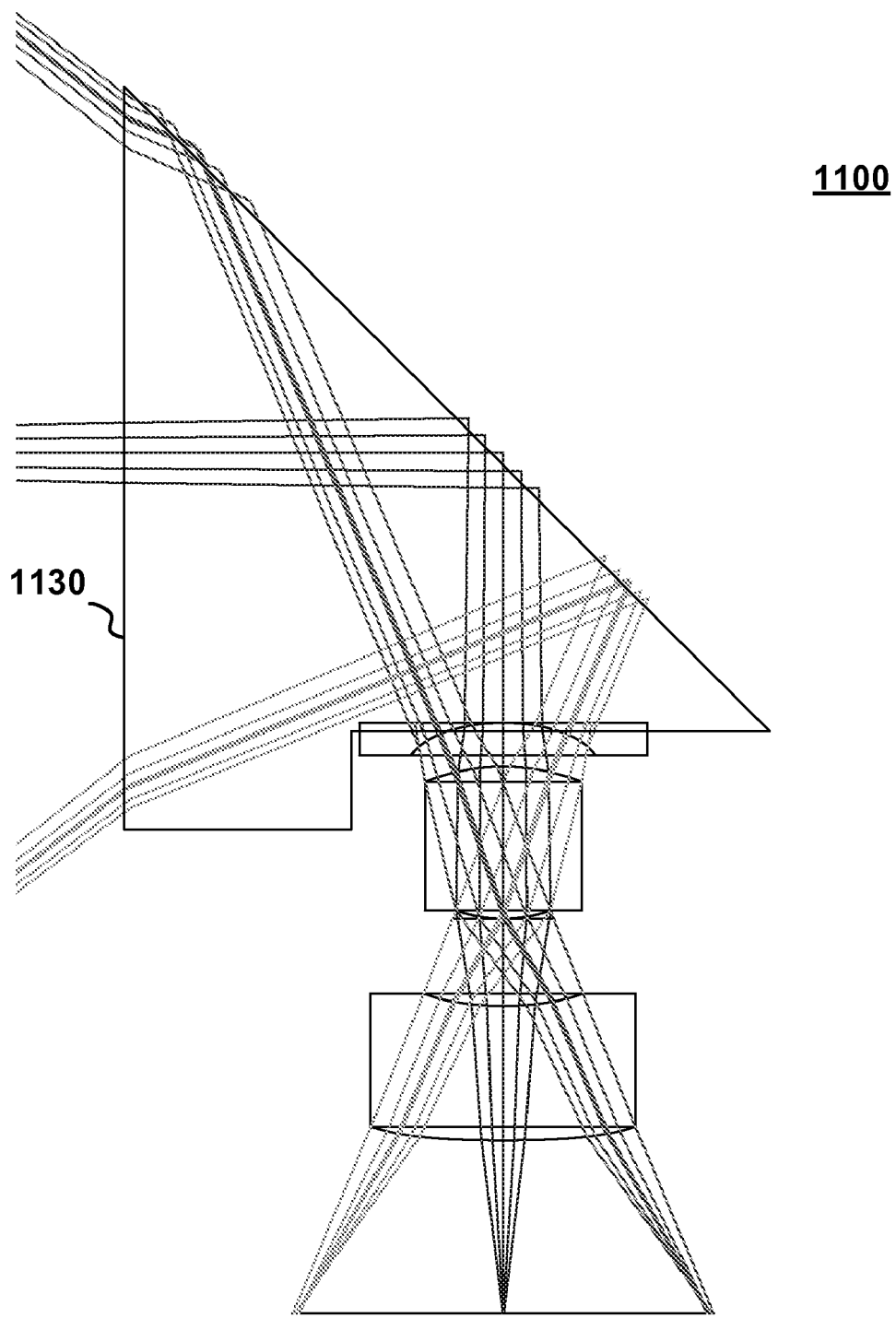
FIG. 11 shows a schematic of a system having one camera and one section of a reflective pyramid wherein the pyramid is immersed in a high-index material according to an aspect of the present invention.

FIG. 11 is a schematic illustration of a single imaging system 1100 and one section of a reflective pyramid 1120 where the pyramid is immersed in a high-index material 1130.

By way of example, the VFOV is 50°, as in our prior-art example in FIG. 4, but Γ is now reduced to 1.3. We may increase the VFOV to 70° with Γ=2.1, still a fraction of the 9.4 value in the prior-art example. Thus, for a given focal length, a larger VFOV can be achieved with a much smaller pyramid according to the present invention.

As can now be appreciated by those skilled in the art, an apparatus constructed accordion to the present invention does not merely reflect or redirect the fields-of-view of a plurality of imagers (cameras) as done in prior art multi camera configurations. Rather, an apparatus according to the present invention is effectively a part of each imager's (camera's) optical objective.

The angles of at least some of the rays, relative to the optical axis, immediately after reflection from a mirror are less than they are in at least a portion of the region between the optical imaging system and the subject object, wherein that portion includes the points where the FOVs of adjacent cameras first overlap. In particular, if the mirror faces are curved, or if the material immersing the pyramid has curvature on either the first or second surface, or both, then the apparatus has optical power and must be considered an integral part of the objective. Finally, all optical systems may be used in reverse as projection systems.

Figure 12:
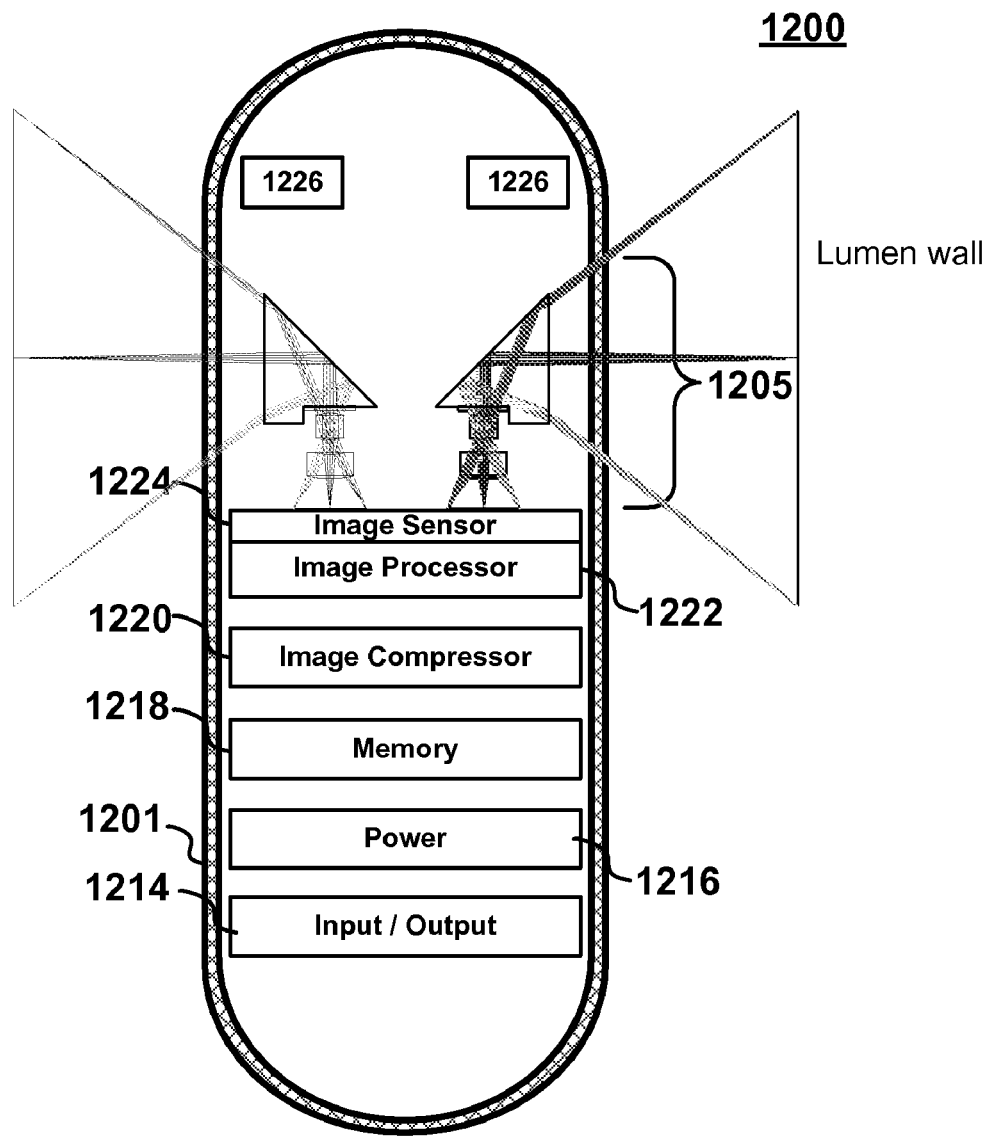
FIG. 12 shows a cross-sectional view of a schematic encapsulated panoramic imaging system including the system of FIG. 12.

An exemplary compact panoramic imaging system according to the principles of the present invention is shown in as a cross-sectional schematic in FIG. 12. For clarity only two imaging systems facing in opposite directions are shown. Those skilled in the art will recognize that the cross-sectional view shown in FIG. 12 may provide a panoramic image throughout a full 360 and is not limited to the apparent image directions shown in the cross sectional view.

As may be further appreciated, devices such as those shown in FIG. 12 are but one of a number of devices that are configured to capture an image from within in vivo passages and cavities within a body, such as those passages and cavities within the gastrointestinal (GI) tract. These devices may comprise a digital camera housed within a capsule along with illuminating light sources. The capsule may be powered by batteries or by inductive power transfer from outside the body. The capsule may also contain memory for storing captured images and/or a radio transmitter for transmitting data to an ex vivo receiver outside of the body.

Such a device was described in U.S. patent application Ser. No. 11/642,275 for an "In Vivo Sensor With Panoramic Camera" filed Dec. 19, 2006 assigned to the assignee of the present invention and is incorporated herein by reference.

With reference to FIG. 12, there is shown an encapsulated panoramic imaging system 1200 comprising a housing 1201 which is suitably shaped such that it may travel in vivo within a body through, for example, an esophagus, stomach, intestine or another interior cavity. The capsule is sized up to a maximum diameter of approximately 1.5 cm and length of 4 cm at the time it is swallowed, although it may expand in a controlled fashion within the body.

As shown in FIG. 12, the system comprises a panoramic imager 1205 such as one of the types described earlier. The system 1200 may included within the housing an image processor 1222, an image compressor 1220, a memory device 1218, a power source 1216, an input/output structures 1214. Illumination sources 1226 are preferably low power illumination devices such as light-emitting diodes providing an appropriate power and wavelength(s) of light to sufficiently illuminate in vivo structures of interest.

At this point, while I have discussed and described my invention using some specific examples, those skilled in the art will recognize that my teachings are not so limited. More specifically, while all examples presented herein use four-sided pyramids, the number of sides could, in principle, be any number greater than one. Also, the inclination of the faces need not be exactly 45°. In addition, and while not specifically illustrated, an immersed reflector configuration having convex mirror faces may be constructed. Also, the reflective surface clear apertures need only be coincident with the faces of a pyramid (or convex-faced pyramid, as described above) and the physical object or objects that these reflective surfaces reside on need not be pyramidal. Finally, a system constructed according to the principles of the present invention may advantageously off-load, or otherwise transmit component images to other systems (i.e., not in-vivo) for subsequent processing and/or assembly into panoramic or other images.

Accordingly, the invention should be only limited by the scope of the claims attached hereto

What is claimed is:

1. A panoramic imaging system comprising:
   a plurality of image capture devices, each having an associated center of perspective; and
   a pyramidal reflective element having a plurality of reflective side facets facing in different directions wherein each one of the reflective side facets folds an optical axis associated with at least one of the image capture devices; wherein each one of the centers of perspective has associated with it a component image wherein the component images associated with adjacent side facets partially overlap;
   such that said component images may be combined into a composite panoramic image and
   one or more immersion media into which the reflective side facets of the pyramidal reflective element are effectively immersed, said immersion media having a characteristic index of refraction n1;
   a further medium into which the immersion media are effectively immersed, said further medium having a characteristic index of refraction n2, wherein n1>n2 for each immersion medium;
   wherein said imaging system includes a plurality of optical paths each of which includes:
       a first refractive interface through which a light ray is bent by a first angular amount followed by;
       a reflective interface followed by;
       a second refractive interface through which the light ray is bent by a second angular amount.

2. The panoramic imaging system of claim 1 wherein said second angular amount is less than or equal to said first angular amount.

3. The panoramic imaging system of claim 1 further comprising an image processing device for combining the component images into a composite panoramic image.

4. The panoramic imaging system of claim 1 wherein one or more of said reflective side facets exhibits a convex shape.

5. A panoramic imaging system comprising:
   a plurality of image capture devices, each having an associated center of perspective; and
   a plurality of reflective surfaces facing in different directions wherein the reflective surfaces are arranged such that their combined shape is substantially pyramidal wherein each one of the reflective surfaces folds an optical axis associated with at least one of the image capture devices; wherein each one of the centers of perspective has associated with it a component image wherein the component images associated with adjacent side facets partially overlap;
   such that said component images may be combined into a composite panoramic image and
   one or more immersion media into which the reflective side facets of the pyramidal reflective element are effectively immersed, said immersion media having a characteristic index of refraction n1;
   a further medium into which the immersion media are effectively immersed, said further medium having a characteristic index of refraction n2, wherein n1>n2 for each immersion medium;
   wherein said imaging system includes a plurality of optical paths each of which includes:
       a first refractive interface through which a light ray is bent by a first angular amount followed by;
       a reflective interface followed by;
       a second refractive interface through which the light ray is bent by a second angular amount.

6. The panoramic imaging system of claim 5 wherein each one of said component images is formed on a common image plane.

7. The panoramic imaging system of claim 6 wherein at least a portion of the image capture devices lie on the common image plane.

8. The panoramic imaging system of claim 5 further comprising an image processing device for combining the component images into a composite panoramic image.

9. The panoramic imaging system of claim 5 wherein one or more of said reflective surfaces exhibits a convex shape.

10. A method of producing a composite panoramic image using a plurality of sensors each having a respective center of perspective and each center of perspective being associated with a particular optical axis, said method comprising the steps of:

for each of the plurality of centers of perspective refracting light corresponding to a particular center of perspective;

redirecting the refracted light by folding the optical axis associated with the refracted light;

further refracting the redirected light; and generating a component image from the further refracted light; and merging the plurality of component images so generated into a panoramic image;

wherein for each center of perspective there is associated one or more individual light rays that are refracted in the first refractive step by a first angular amount and refracted in the second refractive step by a second refractive angular amount wherein the first angular amount is greater than the second angular amount.

* * * * *